(12) United States Patent
Lee et al.

(10) Patent No.: US 7,507,854 B2
(45) Date of Patent: Mar. 24, 2009

(54) IMPURITY REDUCTION IN OLEFIN METATHESIS REACTIONS

(75) Inventors: Choon Woo Lee, La Canada, CA (US); Soon Hyeok Hong, Pasadena, CA (US); Daniel P. Sanders, Pasadena, CA (US); Robert H. Grubbs, South Pasadena, CA (US); Richard L. Pederson, San Gabriel, CA (US)

(73) Assignee: Materia, Inc., Pasadena, CA (US)

( * ) Notice: Subject to any disclaimer, the term of this patent is extended or adjusted under 35 U.S.C. 154(b) by 127 days.

(21) Appl. No.: 10/924,743

(22) Filed: Aug. 23, 2004

(65) Prior Publication Data

US 2005/0203324 A1 Sep. 15, 2005

Related U.S. Application Data

(63) Continuation-in-part of application No. 10/155,854, filed on May 24, 2002, now Pat. No. 6,900,347, and a continuation-in-part of application No. 09/833,018, filed on Apr. 10, 2001, now Pat. No. 6,696,597, which is a continuation-in-part of application No. 09/387,486, filed on Sep. 1, 1999, now Pat. No. 6,215,019.

(60) Provisional application No. 60/293,931, filed on May 24, 2001, provisional application No. 60/098,792, filed on Sep. 1, 1998.

(51) Int. Cl.
C07C 69/52 (2006.01)

(52) U.S. Cl. .................................... 560/205

(58) Field of Classification Search ...................... None
See application file for complete search history.

(56) References Cited

U.S. PATENT DOCUMENTS

| | | | |
|---|---|---|---|
| 3,721,718 A | | 3/1973 | Hughes et al. |
| 4,423,275 A | * | 12/1983 | Myers .......................... 585/645 |
| 4,844,916 A | | 7/1989 | Ogawa et al. |
| 4,923,119 A | | 5/1990 | Yamamoto et al. |
| 5,312,940 A | | 5/1994 | Grubbs et al. |
| 5,342,909 A | | 8/1994 | Grubbs et al. |
| 5,775,026 A | | 7/1998 | Pearce et al. |
| 5,831,108 A | | 11/1998 | Grubbs et al. |
| 5,916,983 A | | 6/1999 | Pederson et al. |
| 5,917,071 A | | 6/1999 | Grubbs et al. |
| 5,969,170 A | | 10/1999 | Grubbs et al. |
| 5,977,393 A | | 11/1999 | Grubbs et al. |
| 6,060,570 A | | 5/2000 | Nubel et al. |
| 6,107,420 A | | 8/2000 | Grubbs et al. |
| 6,111,121 A | | 8/2000 | Grubbs et al. |
| 6,211,391 B1 | | 4/2001 | Grubbs et al. |
| 6,215,019 B1 | | 4/2001 | Pederson et al. |
| 6,225,488 B1 | | 5/2001 | Mukerjee et al. |
| 6,376,690 B1 | | 4/2002 | Grubbs et al. |

2003/0023123 A1 1/2003 Paulson et al.

FOREIGN PATENT DOCUMENTS

| | | |
|---|---|---|
| WO | WO 96/04289 | 2/1996 |
| WO | WO 98/39346 | 9/1998 |
| WO | WO 99/00396 | 1/1999 |
| WO | WO 99/00397 | 1/1999 |
| WO | WO 99/28330 | 6/1999 |
| WO | WO 99/29701 | 6/1999 |
| WO | WO 99/50330 | 10/1999 |
| WO | WO 99/51344 | 10/1999 |
| WO | WO 00/15399 | 3/2000 |
| WO | WO 00/43343 | 7/2000 |
| WO | WO 00/58322 | 10/2000 |
| WO | WO 00/71554 | 11/2000 |

OTHER PUBLICATIONS

Couturier, et al., "A cyclometalated aryloxy(chloro)neopentylidenetungsten complex: a highly active and stereoselective catalyst for the metathesis of cis- and trans-2-pentene, norbornene, 1-methyl-norbornene and ethyl oleate," Angew. Chem. Intl. Ed. Engl. (1992) 31:628.

Ellis, et al., "Water-soluble tris(hydroxymethyl)phosphine complexes with nickel, palladium and platinum, crystal structure of [Pd{P(CH$_2$OH)$_3$}$_4$]=CH$_3$OH," Inorg. Chem. (1992) 31:3026-3033.

Goodwin, et al., "FeCh$_2$P(CH$_2$OH)$_2$: a new, reactive, yet air-stable ferrocene-derived phosphine [Fc=(η-C$_5$H$_5$)FeC$_5$H$_4$]," Chem. Commun. (1996) 1551.

Grubbs, et al., "Recent advances in olefin metathesis and its application in organic synthesis," Tetrahedron (1998) 54:4413-4450.

O'Leary, et al., "A new method for cross-metathesis of terminal olefins," Tetrahedron Lett. (1998) 39:7427.

Scholl, et al., "Synthesis and activity of a new generation of ruthenium-based olefin metathesis catalysts coordinated with 1,3-dimesityl-4,5-dihydro-imidazol-2-ylidene ligands," Org. Lett. (1999) 1:953-956.

Simon, (ed.) "The synthesis of insect pheromones, 1979-1989," The Total Synthesis of Natural Products (Wiley & Sons), 1992, pp. 252-265.

Blackwell, et al., "New approaches to olefin cross-metathesis," J. Am. Chem. Soc. (2000) 122:58-71.

Brandsma, "Preparative Acetylenic Chemistry," 2$^{nd}$ ed. (Elsevier), 1988, pp. 176-177.

ISOM—1999 International Symposium Olefin Metathesis and Related Chemistry: Catalytic Processes for the Next Millenium, Jul. 11-15, 1999, The Netherlands, http://web.mit.edu/rru/isom/level2/contact.htm.

Laurence, et al., "Erythro-6-acetoxy-5-hexadecanolide, the major component of a mosquito oviposition attractant pheromone," Intl. J. Chem. Soc. (Jan. 1982) 59-60.

Maynard, et al., "Purification technique for the removal of ruthenium from olefin metathesis reaction products," Tetrahedron Lett. (1999) 40:4137-4140.

(Continued)

Primary Examiner—Paul A Zucker
(74) Attorney, Agent, or Firm—Isaac M. Rutenberg; Mintz, Levin, Cohn, Ferris, Glovsky and Popeo, P.C.

(57) ABSTRACT

The present invention relates to the use of isomerization inhibitors in olefin metathesis reactions. The inhibitors are low molecular weight organic acids such as formic acid, acetic acid, benzoic acid, and the like.

23 Claims, No Drawings

OTHER PUBLICATIONS

Olagbemiro, et al., "Production of (5R,6S)-6-acetoxy-5-hexadecanolide, the mosquito oviposition pheromone, from the seed oil of the summer cypress plant, *Kochia scoparia* (Chenopodiaceae)," J. Agric. Food Chem. (1999) 47:3411-3415.

Schwab, et al., "Synthesis and applications of $RuCl_2(=CHR)(PR_3)_2$: the influence of the alkylidene moiety on metathesis activity," J. Am. Chem. Soc. (1996) 118:100-110.

Shani, "Integrated pest management using pheromones," Chemtech (1998) 28:30-35.

Coutrot, et al., "5-formyl-δ-valerolactone: a useful synthon for the chiral synthesis of the Vespa orientalis pheromone and the mosquito oviposition attractant pheromone," Tetrahedron Lett. (1994) 45:8381-8384.

Gravier-Pelletier, et al., "Enantiopure hydroxylactones from L-ascorbic and D-isoascorbic acids. Part II. Synthesis of (-)-(5R,6S)-6-acetoxy-5-hexadecanolide and its diastereomers," Tetrahedron (1995) 6:1663-1674.

Howse, et al., "Insect Pheromones and Their Use in Pest Management," (Chapman & Hall), 1998.

Dawson, et al., "Convenient synthesis of mosquito oviposition pheromone and a highly fluorinated analog retaining biological activity," J. Chem. Ecology (1990) 6:1779-1789.

Harris, et al., "Pecan nut casebearer (Lepidoptera: Pyralidae) sex pheromone used to monitor phenology and estimate effective range of traps," J. Econ. Entomol. (1997) 90:983-987.

Henkel, et al., "Lipase-catalyzed synthesis of (5R,6S)-6-acetoxyylkan-5-olides—homologues of the mosquito ovoposition attractant pheromone," J. Prakt. Chem. (1997) 339:434-440.

Laurence, et al., "Absolute configuration of mosquito oviposition attractant pheromone 6-acetoxy-5-hexadecanolide," J. Chem. Ecology (1985) 5:643-648.

Laurence and Pickett, "An oviposition attractant pheromone in Culex quinquefasciatus Say (Diptera: Culicidae)," Bull Entomol. Ref. (1985) 75:283-290.

Millar, "Degradation and stabilization of E8,E10-dodecadienol, the major component of the sex pheromone of the coding moth (Lepidopter: Tortricidae)," J. Econ. Entomol. (1995) 5:1425-1432.

Millar, et al., "Sex attractant pheromone of the pecan nut casebearer (Lepidoptera: Pyralidae)," Bioorg. Med. Chem. (1996) 3:331-339.

Negishi, et al., "Stereoselective synthesis of conjugated trans-enynes readily convertible into conjugated cis, trans-dienes and its application to the synthesis of the pheromone bombykol," J.C.S. Chem. Comm. (1973) 874-875.

Otieno, et al., "A field trial of the synthetic oviposition pheromone with Culex quinquefasciatus say (Diptera: Culicidae) in Kenya," Bull. Entomol. Res. (1988) 78:463-478.

Alexakis, et al., "Z-I-iodohexane," Org. Synth. Coll., vol. 7 (Wiley & Sons), 1990, pp. 290-294.

Bach and Knight, "Epoxidation of olefins by hydrogen peroxide-acetonitrile: cis-cyclooctene oxide," Org. Synth. Coll., vol. 7 (Wiley & Sons), 1990, pp. 126-128.

Ruhoff, "n-Heptanoic acid," Org. Synth. Coll., vol. 2 (Wiley & Sons), 1943, pp. 315-316.

Witzemann, et al., "dl-Glyceraldehyde ethyl acetal," Org. Synth. Coll., vol. 2 (Wiley & Sons), 1943, pp. 307-309.

"Production by the U.S. Chemical Industry," C&E News (Jul. 4, 1994) p. 36.

Mori, "Synthesis of optically active pheromones," Tetrahedron Rept. (1989) 11:3233-3298.

Svirskaya, et al., "Synthesis of pure (9Z,11Z), (9E, 11E) and (9Z, 11E)-9,11-hexadecadienyls—possible candidate pheromones," J. Chem. Ecol. (1984) 5:795-807.

Trnka and Grubbs, "The development of $L_2X_2Ru=CHR$ olefin metathesis catalysts: an organometallic success story," Acc. Chem. Res. (2001) 34:18-29.

Arduengo, et al., "Looking for stable carbenes: the difficulty in starting anew," Acc. Chem. Res. (1999) 32:913-921.

Grayson, "Phosphonium compounds. III. Mechanism of hydroxide cleavage of tetrakis(hydroxymethyl)phosphonium chloride," J. Am. Chem. Soc. (1963) 79-83.

Bourissou, et al., "Stable carbenes," Chem. Rev. (2000) 100:39-91.

Corriu, et al., J. Am. Chem. Commun. (1980) 168:169.

Dervan, et al., "Deoxygenation of epoxides with inversion of stereochemistry," J. Am. Chem. Soc. (1976) 98:1265-1267.

Furstner, et al., "Olefin metathesis and beyond," Angew. Chem. Intl. Ed. (2000) 39:3012-3043.

Huang, et al., "Olefin metathesis-active ruthenium complexes bearing a nucleophilic carbene ligand," J. Am. Chem. Soc. (1999) 121:2674-2678.

Ivin, "Some recent applications of olefin metathesis in organic synthesis: A review," J. Mol. Catal. A—Chem. (1998) 133:1-16.

Jafarpour and Nolan, "Simple and convenient synthetic procedure leading to ruthenium Olefin metathesis catalysts bearing the N,N'-bis(mesityl)imidazol-2-ylidene (IMes) ligand," Oranometallics (2000) 19:2055-2057.

Randall, et al., "New tools for the organic chemist," J. Mol. Catal. A—Chem. (1998) 133:29-40.

Scholl, et al., "Increased ring closing metathesis activity of ruthenium-based olefin metathesis catalysts coordinated with imidazolin-2-ylidene ligands," Tetrahedron Lett., (1999) 40:2247-2250.

Schwab, et al., "A series of well-defined metathesis catalysts—synthesis and applications of $RuCl_2(=CHR')(PR_3)_2$," Angew. Chem. Intl. Ed. Engl. (1995) 34:2039-2041.

Still, "Conjugate addition of trimethysilyllithium. A preparation of 3-silyl ketones," J. Org. Chem. (1976) 41:3063-3064.

Garber, et al., "Efficient and recyclable monomeric and dendritic Ru-based metathesis catalysts," J. Am. Chem. Soc. (2000) 122:8168-8179.

Kingsbury, et al., "A recyclable Ru-based metathesis catalyst," J. Am. Chem. Soc. (1999) 121:791-799.

Chatterjee, et al., "Synthesis of funtionalized olefins by cross and ring-closed metatheses," J. Am. Chem. Soc. (2000) 122:3783-3784.

Bielawski, et al., "Highly efficient ring opening metathesis polymerization (ROMP) using new ruthenium catalysts coordinated with N-heterocyclic carbene ligands," Angew. Chem. Intl. Ed. (2000) 39:2903-2906.

Ivin, et al., "Olefin Metathesis and Metathesis Polymerization," Academic Press, San Diego, 1997, p. 4.

Lehman, et al., "Olefin isomerization induced by well-defined metathesis catalysts," Inorg. Chem. Acta (2003) 345:190-198.

Schmidt, "Catalysis at the interface of ruthenium-carbene and ruthenium hydride chemistry: organometallic aspects and applications to organic synthesis," Eur. J. Org. Chem. (2004) 1865-1880.

Hong, et al., "Decomposition of a key intermediate in ruthenium-catalyzed olefin metathesis reactions," J. Am. Chem. Soc. (2004) 126:7414-7415.

* cited by examiner

IMPURITY REDUCTION IN OLEFIN METATHESIS REACTIONS

CROSS-REFERENCE TO RELATED APPLICATIONS

This is a continuation-in-part of U.S. Ser. No. 10/155,854, filed May 24, 2002 (which issued May 31, 2005, as U.S. Pat. No. 6,900,347), which claimed priority under 35 U.S.C. §119 (e)(1) to provisional U.S. Ser. No. 60/293,931, filed May 24, 2001, and which was also filed as a continuation-in-part of U.S. Ser. No. 09/833,018, filed Apr. 10, 2001 (which issued Feb. 24, 2004 as U.S. Pat. No. 6,696,597), the latter application filed (1) claiming priority to International Application No. PCT/US00/31549, filed Nov. 17, 2000, in turn claiming priority to provisional U.S. Ser. No. 60/166,543, filed Nov. 18, 1999, and (2) as a continuation-in-part of U.S. Ser. No. 09/387,486, filed Sep. 1, 1999 (which issued Apr. 10, 2001 as U.S. Pat. No. 6,215,019) claiming priority under 35 U.S.C. §119(e)(1) to provisional U.S. Ser. No. 60/098,792, filed Sep. 1, 1998. The disclosures of the aforementioned applications are incorporated by reference in their entireties.

TECHNICAL FIELD

The invention relates generally to catalytic olefin metathesis reactions, and more particularly relates to additives used in such reactions to reduce the production of unwanted byproducts and thereby improve the yield and purity of the desired reaction products.

BACKGROUND

To the synthetic organic or polymer chemist, simple methods for forming carbon-carbon bonds are extremely important and valuable tools. "Olefin metathesis," as is understood in the art, is one such method and refers to the metal-catalyzed redistribution of carbon-carbon bonds. See Trnka and Grubbs (2001) *Acc. Chem. Res.* 34:18-29. Over the past decade, olefin metathesis has emerged as a powerful carbon-to-carbon bond-forming reaction that is widely used in organic synthesis and polymer science. This is largely due to the development of certain transition metal alkylidene complexes that have proven to be highly active metathesis catalysts. These catalysts, developed by Robert H. Grubbs at the California Institute of Technology, are described, inter alia, in U.S. Pat. Nos. 5,312,940, 5,342,909, 5,831,108, 5,017,071, 5,969,170, 6,111,121, and 6,211,391 to Grubbs et al., and in Bourissou et al. (2000) *Chem. Rev.* 100:39-91 Trnka and Grubbs (2001), supra. The current "Grubbs catalysts," in which a central ruthenium atom is substituted with an N-heterocyclic carbene ligand, offer many advantages, including readily tunable steric bulk, vastly increased electron donor character, compatibility with a variety of metal species, improved thermal stability, and tolerance of a wide variety of functional groups on the olefinic reactants. See Scholl et al. (1999) *Tetrahedron Lett.* 40:2247-2250; Scholl et al. (1999) *Org. Lett.* 1:953-956; Chatterjee et al. (2000) *J. Am. Chem. Soc.* 122:3783-3784; and Bielawski et al. (2000) *Angew. Chem. Int. Ed.* 39:2903-2906.

The ruthenium metathesis catalysts and derivatives thereof have firmly established olefin metathesis as a versatile and reliable synthetic technique for advanced organic synthesis, and have proven to be useful in connection with a number of different types of metathesis reactions, including cross-metathesis (e.g., ethenolysis), ring-closing metathesis (RCM), ring-opening metathesis (ROM), ring-opening metathesis polymerization (ROMP), and acyclic diene metathesis (ADMET) polymerization. The metathesis reaction products have a variety of uses; for example, alpha olefins are useful in the preparation of poly(olefin) polymers, alpha, omega ester-functionalized olefins can be converted to thermoset polymers such as epoxy resins and polyurethanes, and the like. As with any commercially significant chemical processes, however, there is an ongoing interest in improving the purity and yield of the reaction product.

In olefin metathesis, olefin isomerization is one of the side reactions observed that can significantly alter the product distribution and decrease the yield of the desired product, especially with ill-defined catalyst systems. (Ivin, K. J.; Mol, J. C. *Olefin Metathesis and Metathesis Polymerization*; Academic Press: San Diego, Calif., 1997; p 4.) Additionally, the side products resulting from unwanted isomerization are frequently difficult to separate via standard techniques. Well-defined ruthenium-based olefin metathesis catalysts are generally highly selective for olefin metathesis; however, there have been some reports of olefin isomerization occurring with these catalysts as well. See, e.g., Lehman et al. (2003) *Inorg Chim. Acta* 345:190-198; Schmidt (2004). *Eur. J. Org. Chem,* 1865-1880, and references cited therein.) Recently, the Grubbs group has shown that ruthenium hydride species formed from decomposition of catalysts could be responsible for the undesirable isomerization reaction. Hong et al. (2004). *J. Am. Chem. Soc.* 126:7414-7415. This information has allowed for the development of additives to block the unwanted isomerization reaction by scavenging metal hydrides from decomposed ruthenium catalysts, which, in turn, improves reaction products yields and purities.

Paulson and Pederson, in U.S. Patent Publication No. 2003/0023123 A1, described the use of (1) low temperature reaction conditions, and (2) halogenated alkanes, halogenated aromatics, quinones, halogenated quinones, BHT, and vitamin E as isomerization inhibitors, in order to increase purity in metathesis reactions. There is nevertheless an ongoing need for additional isomerization inhibitors that increase the purity and yield of desired metathesis products.

SUMMARY OF THE INVENTION

The present invention describes the use of acidic isomerization inhibitors in olefin metathesis reactions to reduce unwanted reaction products resulting from olefin isomerization, thereby significantly improving yields and greatly reducing impurities.

In one embodiment, the invention provides a method for carrying out an olefin metathesis reaction, comprising contacting at least one olefinic reactant with an olefin metathesis catalyst at a temperature in the range of −72° C. to about 20° C. in the presence of an effective amount of an isomerization inhibitor.

The invention, in a further embodiment, provides a method for carrying out an ethenolysis reaction, comprising contacting ethylene and at least one additional olefinic reactant with an olefin metathesis catalyst at a temperature in the range of −72° C. to about 20° C. in the presence of a quinone, a substituted quinone, BHT, vitamin E, and/or an organic acid having the formula $R^{10}$—COOH where $R^{10}$ is selected from H, $C_1$-$C_6$ alkyl, $C_2$-$C_6$ alkenyl, halogenated $C_1$-$C_6$ alkyl, halogenated $C_1$-$C_6$ alkenyl, phenyl, halogenated phenyl, benzyl, and halogenated benzyl, wherein the organic acid is present in an amount effective to inhibit olefin isomerization.

The invention, in a further embodiment, provides a method for carrying out an olefin metathesis reaction, comprising contacting an α-olefin and at least one additional olefinic reactant with an olefin metathesis catalyst at a temperature in the range of −72° C. to about 20° C. in the presence of a quinone, a substituted quinone, BHT, vitamin E, and/or an organic acid having the formula $R^{10}$—COOH where $R^{10}$ is selected from H, $C_1$-$C_6$ alkyl, $C_2$-$C_6$ alkenyl, halogenated $C_1$-$C_6$ alkyl, halogenated $C_1$-$C_6$ alkenyl, phenyl, halogenated phenyl, benzyl, and halogenated benzyl, wherein the organic acid is present in an amount effective to inhibit olefin isomerization.

Preferred organic acids are low molecular weight carboxylic acids. Also preferred are organic acids having a pKa in the range of about 1.5 to about 6.5.

The invention is useful in a variety of metathesis reactions, including intramolecular reactions such as ring-closing metathesis and cross-metathesis reactions such as ethenolysis. The invention is particularly useful in ethenolysis processes, e.g., to convert F renewable seed oils into alpha olefins and unsaturated acids and esters, preferably alpha, omega-unsaturated acids and esters. Alpha olefins are valuable starting monomers in the preparation of polyolefin polymers. Alpha, omega-unsaturated acids and esters can be converted by well known chemical techniques, e.g. transesterifications, epoxidations, hydroformylations, hydrocyanations, reductive amination, and the like into ester-epoxide monomers, ester-alcohol monomers, diol monomers, and ester-amine monomers, any of which can be polymerized to yield useful products. Poly(ester epoxides) find utility, inter alia, in the manufacturing of epoxy thermoset resins. Poly(ester alcohols), poly diols, poly(ester amines) and poly(amino alcohols) are recognized as having utility in the manufacturing of polyurethanes.

The techniques of this invention are useful in conjunction with a wide range of olefin metathesis catalysts, including Grubbs' bis phosphine catalysts, Grubbs' N-heterocyclic carbene-substituted rutheniuim catalysts, and the like, including but not limited to those that are useful in catalyzing metathesis reactions for synthesizing methyl 5-hexenoate, methyl 9-decenoate, methyl 11-dodecenoate, 5-hexenoic acid, 9-decenoic acid, 11-dodecenoic acid, 1-decene, 1-hexadecene, 1-octadecene, 2,5-dihydrofuran and methyl 5-t-butyldimethylsilyoxy-2-pentenoate.

DETAILED DESCRIPTION OF THE INVENTION

The present invention describes isomerization inhibitors that significantly improve product yields and purity in olefin metathesis reactions. The invention may be applied to any catalytic olefin metathesis reaction to obtain yield enhancement and impurity reduction.

As an initial matter, "olefin metathesis," as it is understood in the art, refers to the metal-catalyzed redistribution of carbon-carbon bonds in a reaction involving an olefin. While the invention is broadly applicable to almost all reactions involving olefin metathesis catalysts, some of these catalysts are better known than others. Among the catalysts of interest are the neutral ruthenium or osmium metal carbene complexes that possess metal centers that are formally in the +2 oxidation state, have an electron count of 16, and are penta-coordinated. Other catalysts of particular interest include, but are not limited to, cationic ruthenium or osmium metal carbene complexes that possesses metal centers that are formally in the +2 oxidation state, have an electron count of 14, and are tetra-coordinated. Examples of such metathesis catalysts have been previously described in, for example, U.S. Pat. Nos. 5,312,940, 5,342,909, 5,831,108, 5,017,071, 5,969,170, 6,111,121, and 6,211,391 to Grubbs et al., and in Bourissou et al. (2000), Trnka and Grubbs (2001), Scholl et al. (1999) Tetrahedron Lett. 40:2247-2250, Scholl et al. (1999) Org. Lett. 1:953-956, Chatterjee et al. (2000), and Bielawski et al. (2000), all cited previously herein.

The aforementioned ruthenium and osmium carbene complexes are of the general formula (I):

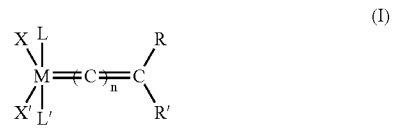

where n=0 to 2, M is a Group 8 transition metal such as ruthenium or osmium, X and X' are anionic ligands, L and L' are neutral electron donors, and R and R' are specific substituents, e.g., one may be H and the other may be a substituted silyl, substituted, or unsubstituted hydrocarbyl group such as phenyl or —C═C($CH_3$)$_2$. Such complexes have been shown to be useful in catalyzing a variety of olefin metathesis reactions, including ethenolysis, ring opening metathesis polymerization ("ROMP"), ring closing metathesis ("RCM"), acyclic diene metathesis polymerization ("ADMET"), ring-opening metathesis ("ROM"), and cross-metathesis ("CM" or "XMET") reactions. The catalysts' broad range of applications is due in large part to their excellent compatibility with various functional groups and relatively high tolerance to moisture, air, and other impurities (Schwab et al. (1995) Angew. Chem., Int. Ed. Engl. 34:2039-2041; Schwab et al. (1996) J. Am. Chem. Soc. 118:100-110; Ivin (1998) J. Mol. Cat. A-Chem. 133:1-16; Grubbs et al. (1998) Tetrahedron 54:4413-4450; and Randall et al. (1998) J. Mol. Cat. A-Chem. 133:29-40). As has been recognized by those in the field, however, the compounds display low thermal stability, decomposing at relatively low temperatures. See, e.g., Jafarpour et al. (2000) Organometallics 19(11):2055-2057.

For the most part, such metathesis catalysts have been prepared with phosphine ligands, e.g., tricyclohexylphosphine or tricyclopentylphosphine, exemplified by the well-defined, metathesis-active ruthenium alkylidene complexes (II) and (III):

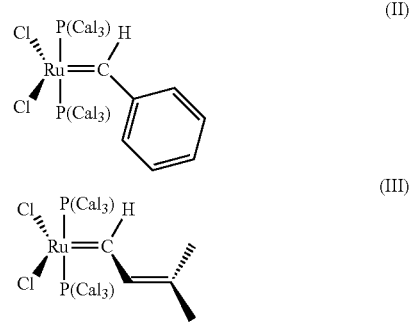

wherein "Cal" is a cycloalkyl group such as cyclohexyl or cyclopentyl. See Grubbs et al., U.S. Pat. No. 5,917,071 and Trnka et al., supra. Replacement of one of the phosphine ligands with a 1,3-disubstituted-4,5-dihydro-(4,5-disubstituted)-imidazole-2-ylidene, such as 1,3-dimesityl-4,5-dihydroimidazol-2-ylidene results in a more active catalyst because of the more electron-rich ruthenium metal center (Scholl et al. (1999), Tetrahedron Letter 40:2247-2200 and Scholl et al. (1999), *Org. Lett.* 1:953-956). Four representative second generation catalysts are the ruthenium complexes (IVA), (IVB), (VA) and (VB):

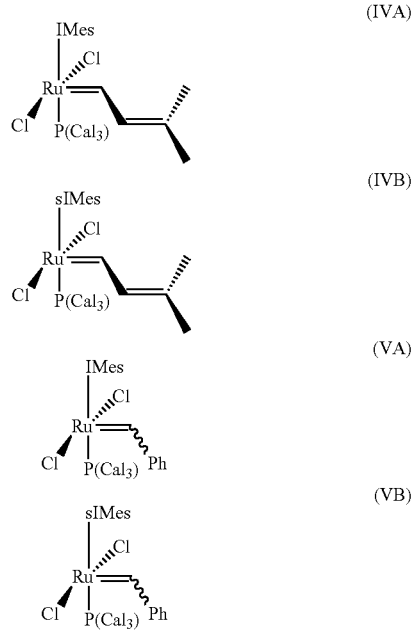

In the above structures, "Cal" is as defined previously, "Ph" represents phenyl, "IMes" represents 1,3-dimesityl-imidazol-2-ylidene:

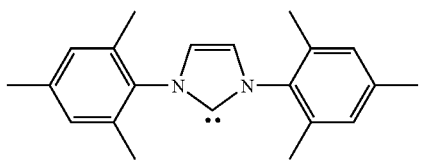

and "sIMes" represents 1,3-dimesityl-4,5-dihydroimidazol-2-ylidene:

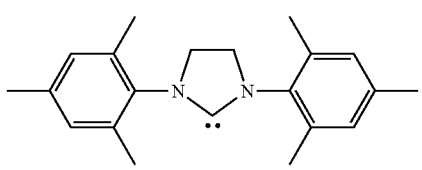

and "N-IMes" represents 1,3-dimesityl-triazolylidene:

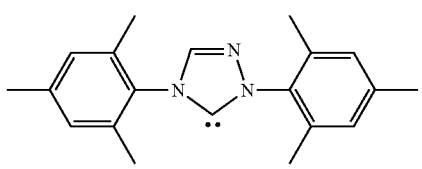

Other complexes formed from N-heterocyclic carbene ligands are also known. These transition metal carbene complexes, particularly those containing a ligand having the 4,5-dihydroimidazol-2-ylidene structure such as in sIMes, have been found to address a number of previously unsolved problems in olefin metathesis reactions, particularly cross-metathesis reactions.

All of the foregoing catalysts, and other olefin metathesis catalysts, may be used in accordance with the invention.

The prior art teaches that olefin metathesis catalysts must be heated for activation to initiate metathesis reactions. It has recently been found that this approach generally renders the metathesis catalyst, including the second generation Grubbs catalysts, too aggressive in their activity, see U.S. Patent Publication No. 2003/0023123 A1. As in the aforementioned patent publication, the present methods and systems are preferably conducted at a low temperature. For the N-heterocyclic carbene catalysts, reaction temperatures that will assist in impurity reduction are in the range of about of about −72° C. to about 20° C., more preferably in the range of about −72° C. to about 10° C., most preferably in the range of about −5° C. to about 10° C., and optimally in the range of about 5° C. to about 10° C.

Unless otherwise indicated, the term "yield" refers to reaction product and the term "conversion" refers to reactants consumed in the reaction. In particular, percent conversion is calculated by determining the amount (mass or moles) of a reactant consumed as a percentage of the amount (mass or moles) of that reactant initially present before reaction commenced. Since many metathesis reactions are equilibrium reactions that do not go to a final endpoint so as to consume all reactants but can nonetheless be driven to consume one reactant by adding an excess of another, the theoretical or calculated yield of reaction product is dependent on the proportions of reactants, if more than one olefin is present. Thus, for a reaction consuming equimolar amounts of two reactants, where equal molar amounts of reactants are present initially, the yield may be derived from the conversion of either of the reactants. For example, if one mole of each reactant is needed to produce one mole of product, and 0.8 moles of each reactant was consumed out of 1.2 moles of each initially present (either due to equilibrium, or due to stopping of the reaction), and 0.6 moles of product was produced, then the percent yield is 100(0.6/0.8)=75% and the percent conversion is 100(0.8/1.2)=66.67%. In the event one of the reactants is present in excess to drive the reaction beyond the conversion achieved with equimolar amounts of the reactants, then conversion and yield are based on the reactant of which a greater proportion is consumed (i.e. has lowest initial amount present). For example, if reactants A and B combine in equimolar amounts to form C, and there are 5.0 moles of reactant A and 2.5 moles of reactant B present before reaction, then, at equilibrium, after reaction, or when the reaction is stopped, there are 3.0 moles of A remaining and 0.5 moles of B (i.e. 2.0 moles of A were consumed) and 1.8 moles of C. The percent conversion of A is 100(2.0/2.5)=80%, and the percent yield of C is 100(1.8/2.0)=90%. In a ring-opening or ring-closing reaction, in which A converts to B, and one mole of A produces one mole of B, the percent conversion is 100 (moles of A consumed/moles of A present before reaction) and the percent yield is 100 (moles of B produced/moles of A consumed). If no impurities are produced, the theoretical yield of 100% is achieved.

The invention provides yields that approach the theoretical yields quite closely. Thus, in accordance with the invention, the yield is within 10%, preferably 0 to 5% of the theoretically calculated yield. For example, if the theoretical yield is 40% based on reactants consumed, then the actual yield is greater than 30% (within 10%), and is preferably greater than 35% (within 5%).

The metathesis reactions are run neat (i.e. without solvent) to maximize reactor space efficiency. Using an excess of one starting material will increase the yield of product but decrease the time throughput yield.

The isomerization inhibitors herein decrease the rates of reactions that produce undesirable byproducts, also known as impurities. An impurity is regarded as present in an "insignificant" amount if it is present in a small amount and is relatively easily removed. When prior art metathesis reactions are carried out in a solvent-free environment, for example, not in a methylene chloride solution as is typically done, then there is typically the formation of a substantial amount of undesirable impurities such as those due to double bond migration. The compounds that represent such impurities can undergo further metathesis reactions to produce a compound with one carbon less and one carbon more than the desired product. This process can repeat until an equilibrium mixture of impurities is obtained. According to one aspect of the invention, such impurities can be reduced or eliminated by adding an organic acid, a quinone, a substituted quinone (e.g., a halogenated quinone), BHT (butylated hydroxytoluene), or vitamin E as an isomerization inhibitor to the reaction. The organic acid has a pKa in the range of about 1.5 to about 6.5, preferably in the range of about 3.0 to about 4.8, and a molecular weight less than 250 g/mole, preferably less than 175 g/mole. Preferred such acids are of the formula $R^{10}$—COOH where $R^{10}$ is selected from H, $C_1$-$C_6$ alkyl, $C_2$-$C_6$ alkenyl, halogenated $C_1$-$C_6$ alkyl, halogenated $C_1$-$C_6$ alkenyl, phenyl, halogenated phenyl, benzyl, and halogenated benzyl. Examples of such acids include, without limitation, formic acid, acetic acid, benzoic acid, acrylic acid, and dichloroacetic acid. Two or more such organic acids can also be used in combination. Additionally, other isomerization inhibitors can be used in combination with the organic acid(s), including antioxidants such as quinone, halogenated quinones, compounds bearing some similarity to quinone, such as BHT (butylated hydroxytoluene), and Vitamin E. The amount of the isomerization inhibitor(s) used range from about 0.009 mole to 500 mol per mole of catalyst, typically 2 mole per mole of catalyst.

In general, the metathesis catalysts of most interest include, but are not limited to, neutral ruthenium or osmium metal carbene complexes discussed previously, i.e., those that possess metal centers that are formally in the +2 oxidation state, have an electron count of 16, are penta-coordinated, and are of the general formula I, shown below. Other catalysts of particular interest include, but are not limited to, cationic ruthenium or osmium metal carbene complexes that possesses metal centers that are formally in the +2 oxidation state, have an electron count of 14, are tetra-coordinated, and are of the general formula II.

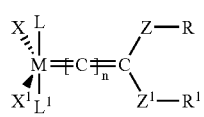

(I)

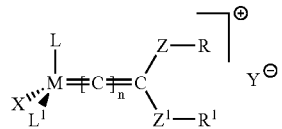

(II)

wherein:
M is ruthenium or osmium;
n is an integer in the range of 0 to 5 inclusive;
L and $L^1$ are each independently any neutral electron donor ligand;
R, $R^1$, and $R^2$ are each independently hydrogen or any hydrocarbyl or silyl moiety,
X and $X^1$ are each independently any anionic ligand;
Y is any non coordinating anion;
Z and $Z^1$ are each independently any linker selected from the group nil, —O—, —S—, —$NR^2$—, —$PR^2$—, —P(=O)$R^2$—, —P($OR^2$)—, —P(=O)($OR^2$)—, —C(=O), —C(=O)O—, —OC(=O), —OC(=O)O—, —S(=O), or —S(=O)$_2$—; and wherein any two or more of X, $X^1$, L, $L^1$, Z, $Z^1$, R, $R^1$, and $R^2$ may be optionally joined together to form a multidentate ligand and wherein any one or more of X, $X^1$, L, $L^1$, Z, $Z^1$, R, $R^1$, and $R^2$ may be optionally linked chemically to a solid or glassy support.

In preferred embodiments of these catalysts, L and $L^1$ are each independently selected from the group consisting of phosphine, sulfonated phosphine, phosphite, phosphinite, phosphonite, arsine, stilbine, ether, amine, amide, imine, sulfoxide, carbonyl, carboxyl, isocyanide, nitrosyl, pyridine, quinoline, thioether, and nucleophilic heterocyclic carbenes of the general formula III:

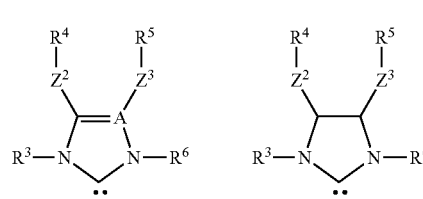

III wherein:
A is either carbon or nitrogen;
$R^3$, $R^4$, $R^5$, and $R^6$ are each independently hydrogen or any hydrocarbyl moiety, except that in the case where A is nitrogen $R^5$ is nil;
$Z^2$ and $Z^3$ are each independently any linker selected from the group nil, —O—, —S—, $NR^2$—, —$PR^2$—, —P(=O)$R^2$—, —P($OR^2$), —P(=O)($OR^2$)—, —C(=O), —C(=O)O—, —OC(=O), —OC(=O)O—, —S(=O), or —S(=O)$_2$—, except that in the case where A is nitrogen $Z^3$ is nil; and $Z^2$, $Z^3$, $R^4$, and $R^5$ together may optionally form a cyclic optionally substituted with one or more moieties selected from the group consisting of $C_1$-$C_{10}$ alkyl, $C_1$-$C_{10}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In some catalysts of interest, L and $L^1$ are each a phosphine of the formula $PR^7R^8R^9$, where $R^7$, $R^8$, and $R^9$ are each independently any hydrocarbyl moiety, particularly aryl, primary $C_1$-$C_{10}$ alkyl, secondary alkyl or cycloalkyl. In certain other embodiments, L and $L^1$ are selected from the group consisting of —P(cyclohexyl)$_3$, —P(cyclopentyl)$_3$, —P(isopropyl)$_3$, —P(butyl)$_3$, and —P(phenyl)$_3$.

In the embodiments of most interest, L is a phosphine and L1 is a nucleophilic carbene of the general formula III. Preferably, L is selected from the group consisting of —P(cyclohexyl)$_3$, —P(cyclopentyl)$_3$, —P(isopropyl)$_3$, —P(butyl)$_3$, and —P(phenyl)$_3$ and $L^1$ is selected from the group consisting of:

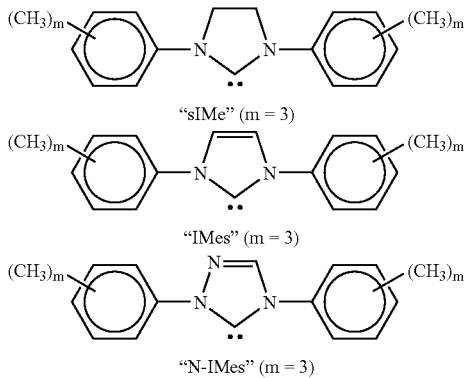

wherein m is an integer in the range of 0 to 5 inclusive.

Relating to R and $R^1$-$R^9$, examples of hydrocarbyl moieties include, but are not limited to, $C_1$-$C_{20}$ alkyl, $C_3$-$C_{20}$ cycloalkyl, $C_2$-$C_{20}$ alkenyl, $C_2$-$C_{20}$ alkynyl, aryl, heteroaryl, aralkyl, and alkaryl. Examples of silyl moieties include, but are not limited to, tri(hydrocarbyl)silyl, tri(hydrocarbyloxy)silyl, and mixed (hydrocarbyl)(hydrocarbyloxy)silyl. Optionally, each of the R, $R^1$, and $R^2$ substituent groups may be substituted with one or more hydrocarbyl or silyl moieties, which, in turn, may each be further substituted with one or more groups selected from halogen, $C_1$-$C_5$ alkyl, $C_1$-$C_5$ alkoxy, phenyl, and substituted phenyl. Moreover, any of the catalyst ligands may further include one or more functional groups. Examples of suitable functional groups include, but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. In addition, any or all of L, $L^1$, R, $R^1$ and $R^2$ may be joined to form a bridging or cyclic structure.

In embodiments of particular interest, the R substituent is hydrogen and the $R^1$ substituent is selected from the group consisting of $C_1$-$C_{20}$ alkyl, $C_2$-$C_{20}$ alkenyl, aryl, alkaryl, aralkyl, trialkylsilyl, and trialkoxysilyl. In certain preferred embodiments, n equals 0, 1 or 2, and the $R^1$ substituent is phenyl, t-butyl, or vinyl, optionally substituted with one or more moieties selected from the group consisting of $C_1$-$C_5$ alkyl, $C_1$-$C_5$ alkoxy, phenyl, and a functional group. In especially preferred embodiments, n equals 0 or 1 and $R^1$ is phenyl, t-butyl, or vinyl substituted with one or more moieties selected from the group consisting of chloro, bromo, iodo, fluoro, —NO$_2$, —NMe$_2$, methyl, methoxy, and phenyl.

In some embodiments of interest, X and $X^1$ are each independently hydrogen, halide, or one of the following groups: $C_1$-$C_{20}$ alkyl, aryl, $C_1$-$C_{20}$ alkoxide, aryloxide, $C_3$-$C_{20}$ alkyldiketonate, aryldiketonate, $C_1$-$C_{20}$ carboxylate, arylsulfonate, $C_1$-$C_{20}$ alkylsulfonate, $C_1$-$C_{20}$ alkylthiol, aryl thiol, $C_1$-$C_{20}$ alkylsulfonyl, or $C_1$-$C_{20}$ alkylsulfinyl. Optionally, X and $X^1$ may be substituted with one or more moieties selected from the group consisting of $C_1$-$C_{10}$ alkyl, $C_1$-$C_{10}$ alkoxy, and aryl which in turn may each be further substituted with one or more groups selected from halogen, $C_1$-$C_5$ alkyl, $C_1$-$C_5$ alkoxy, and phenyl. In more preferred embodiments, X and $X^1$ are halide, benzoate, $C_1$-$C_5$ carboxylate, $C_1$-$C_5$ alkyl, phenoxy, $C_1$-$C_5$ alkoxy, $C_1$-$C_5$ alkylthiol, aryl thiol, aryl, and $C_1$-$C_5$ alkyl sulfonate. In certain preferred embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, X and $X^1$ are each chloro, bromo, or iodo. In addition, X and $X^1$ together may comprise a bidentate ligand.

Y may be derived from any tetra-coordinated boron compound or any hexa-coordinated phosphorus compound. Preferred boron compounds include $BF_4^-$, $BPh_4^-$, and fluorinated derivatives of $BPh_4^-$, but others are also useful. Preferred phosphorous compounds include, but are not limited to, $PF_6^-$ and $PO_4^{-2}$. The non-coordinating anion may be also any one of the following: $ClO_4^-$, $SO_4^=$, $NO_3^-$, $OTeF_5^-$, $F_3CSO_3^-$, $H_3CSO_3^-$, $CF_3COO^-$, $PhSO_3^-$, or $(CH_3)C_6H_5SO_3^-$. Y may be also derived from carboranes, chloro borates, carborane anions, fullerides, aluminoxanes, and the like.

The catalyst:olefin monomer ratio in the invention is preferably between about 1:5 and about 1:1,000,000. More preferably, the catalyst:olefin ratio is about 1:1 to 1:200, or conforms with the literature, which usually puts the ratio in the range between about 1:10 and about 1:10,000 and, most preferably, between about 1:20 and about 1:1,000 or about 1:20 to 1:100.

Particularly preferred metal catalysts include, but are not limited to: (PCy$_3$)Cl$_2$Ru=CHPh, (PCy$_3$)Cl$_2$Ru=CH—CH=CMe$_2$, (PCy$_3$)Cl$_2$Ru=C=CHCMe$_3$, (PCy$_3$)Cl$_2$Ru=C=CHSiMe$_3$, (PCy$_3$)(s-IMes)Cl$_2$Ru=CH—CH=CMe$_2$, (PCP$_3$)$_2$Cl$_2$Ru=CH—CH=CMe$_2$, (PCp$_3$)$_2$Cl$_2$Ru=C=CHPh, (PCP$_3$)(s-IMes)Cl$_2$Ru=CH—CH=CMe$_2$, (PPh$_3$)(s-IMes)Cl$_2$Ru=C=CHCMe$_3$, (PPh$_3$)Cl$_2$Ru=C=CHSiMe$_3$, (PPh$_3$)Cl$_2$Ru=C=CHCMe$_3$, (P(i-Pr)$_3$)Cl$_2$Ru=C=CHPh, (PPh$_3$)(s-IMes)Cl$_2$Ru=C=CHSiMe$_3$, (PBu$_3$)$_2$Cl$_2$Ru=C=CHPh, (PPh$_3$)(s-IMes)Cl$_2$Ru=CH—CH=CMe$_2$, (PCy$_3$)(s-IMes)Cl$_2$Ru=C=CHPh, (PCp$_3$)(s-IMes)Cl$_2$Ru=C=CHPh, (PBu$_3$)(s-IMes)Cl$_2$Ru=C=CHPh, (PCy$_3$)(s-IMes)Cl$_2$Ru=CHPh, (PBu$_3$)(s-IMes)Cl$_2$Ru=CH—CH=CMe$_2$, (PCy$_3$)(IMes)Cl$_2$Ru=CH—CH=CMe$_2$, (PCp$_3$)(IMes)Cl$_2$Ru=CH—CH=CMe$_2$, (PPh$_3$)(IMes)Cl$_2$Ru=C=CHCMe$_3$, (PPh$_3$)(IMes)Cl$_2$Ru=C=CHSiMe$_3$, (PPh$_3$)(IMes)Cl$_2$Ru=CH—CH=CMe$_2$, (PCy$_3$)(IMes)Cl$_2$Ru=C=CHPh, (PCp$_3$)(IMes)Cl$_2$Ru=C=CHPh, (PBu$_3$)(IMes)Cl$_2$Ru=C=CHPh, (PCy$_3$)(IMes)Cl$_2$Ru=CHPh, (PBU$_3$)(IMes)Cl$_2$Ru=CH—CH=CMe$_2$, (PCy$_3$)(IMes)Cl$_2$Ru=C=CHCMe$_3$, (PCy$_3$)ClRu=CHPh(o-O-Isop), (PCp$_3$)ClRu=CHPh(o-O-Isop), (PPh$_3$)ClRu=CHPh(o-O-Isop), (PBu$_3$)ClRu=CHPh(o-O-Isop), (s-IMes)ClRu=CHPh(o-O-Isop), (IMes)ClRu=CHPh(o-O-Isop), (N-s-IMes)ClRu=CHPh(o-O-Isop), and (N-IMes)ClRu=CHPh(oO-Isop), (s-IiPrPh)ClRu=CHPh(o-O-Isop). Where (o-O-Isop) is ortho-isopropoxyphenyl methylene and s-IiPrPh is bis 1,3-(2,6-diisopropyl phenyl)4,5-dihydroimidazol-2-ylidene.

For convenience and reference herein, various examples of metathesis catalysts are identified by their molecular weight; ruthenium (II) dichloro(3-methyl-1,2-butenylidene) bis(tricyclopentylphosphine) (716); ruthenium (11) dichloro(3-methyl-1,2-butenylidene)bis(tricyclohexylphosphine) (801); ruthenium (II) dichloro (phenylmethylene)bis(tricyclohexylphosphine) (823); ruthenium (II) [1,3-bis-(2,4,6-trimethylphenyl)-2-imidazolidinylidene] dichloro(phenylmethylene)(tricyclohexylphosphine) (848); ruthenium (II) [1,3-bis-(2,4,6-trimethylphenyl)-2-imidazolidinylidene) dichloro(o-isopropoxyphenylmethylene) (627); ruthenium (H) [bis 1,3-(2,6-diisopropyl phenyl)4,5-dihydroimidazol-2-ylidene) dichloro(o-isopropoxyphenylmethylene) (712); ruthenium (II) [1,3-bis-(2,4,6-trimethylphenyl)-2-imidazolidinylidene) dichloro(phenylmethylene)(triphenylphosphine) (830), and ruthenium (II) dichloro(vinyl phenylmethylene)bis(tricyclohexylphosphine) (835); ruthenium (II) dichloro (tricyclohexylphosphine)(o-isopropoxyphenylmethylene) (601), and ruthenium (II) (1,3-bis-(2,4,6,-trimethylphenyl)-2-imidazolidinylidene)dichloro(phenylmethylene)(bis 3-bromopyridine (884)). This molecular weight-based nomenclature will be used the examples that follow.

Examples of unsaturated fatty acid feed stocks and unsaturated fatty acid seed oils suitable for ethenolysis are, but not limited to: 2-butenoic acid, 2-pentenoic acid, 2,4-hexadienoic acid, 3-hexenoic acid, 2-heptenoic acid, 2-octenoic acid, 2-noneoic acid, 4-decenoic acid, 3-dodecenoic acid, 3-tridecenoic acid, 9-tetradecenoic acid, 9-hexadecenoic acid, 6-octadecenoic acid, 9-octadecenoic acid (oleic acid), 9,12-octadecadienoic acid, 9,11-octadecadienoic acid, 9,12,15-octadecatrienoic acid, 5-eicosenoic acid, 9-eicosenoic acid, 11-docosenoic acid, 13-docosenoic acid, 21-triacontenoic acid, and 12-hydroxy-9-actadecenoic acid and like acids. The preferred unsaturated fatty acids are 9-octadecenoic acid (oleic acid), 9,12-octadecadienoic acid (linoleic acid) and 9,11-octadecadienoic acid (conjugated linoleic acid).

The following examples merely serve to illustrate certain aspects of the invention for ease of explanation and are not to be construed as in any way limiting the scope of the invention as described and claimed herein.

EXPERIMENTAL (Z)-5-tert-butyldimethylsilyloxy-2-pentenoate (Herold, P.; Mohr, P.; Tamm, C. *Helv. Chim. Acta*. 1983, 66, 744-754), (Z) 1,4-Bis(tert-butyldimethylsilyloxy)$_2$-butene (Jones, K.; Storey, J. M. D. *Tetrahedron*, 1993, 49, 4901-4906) and 11-eicosenyl acetate (Pederson, R. L.; Fellow, I. M.; Ung, T. A.; Ishihara, H.; Hajela, S. P.; *Adv. Synth. Catal.* 2002, 344, No. 6+7, 728-734) were prepared according to literature procedures. Diallyl ether was purchased from Aldrich and used as received. Methyl oleate was purchased from Nu-Chek Prep (Elysian, Minn.). Meadowfoam oil methyl esters were produced by transesterification of Meadowfoam oil. $CD_2Cl_2$ was dried by distillation from $CaH_2$. NMR spectra were recorded on a Varian Mercury 300 (299.817 MHz for $^1H$).

Starting materials and products were characterized by comparing peaks with known standards, in conjunction with supporting data from gas chromatography retention times (GC-Agilent 6890) and mass spectrum analysis using a mass spectrum detector (GC-MS-Agilent 5973N). Both instruments contained the same column and used the same method for characterizations: column: HP-5 30 m×0.25 mm (ID)× 0.25 μm film thickness. Manufacturer: Agilent; GC and GC-MS method conditions:

Injector temperature: 250° C.

Oven temperature:
Starting temperature: 100° C., hold time: 1 minute.
Ramp rate 10° C./min to: 250° C., hold time: 24 minute.
Carrier gas: Helium
Mean gas velocity: 31.3±3.5% cm/sec (calculated).
Split ratio: ~50:1
GC 6890 FID Detector General Experimental Procedure for Examples 1-3

Substrate (0.16 mmol) and isomerization inhibitor (0.1~1.0 equiv) were dissolved in $CD_2Cl_2$ (0.7 mL) in a 5 mL vial in a nitrogen-filled Vacuum Atmospheres drybox ($O_2$<2.5 ppm). Catalyst C848 (5 mol %) was added to the solution, and the reaction mixture was transferred to an NMR tube fitted with a screw cap. The NMR tube was taken out of the drybox, and heated to 40° C. in an oil bath. The reaction was monitored by $^1H$ NMR.

Example 1

Self-metathesis reaction of (Z)-5-t-butyldimethylsilyloxy-2-pentenoate

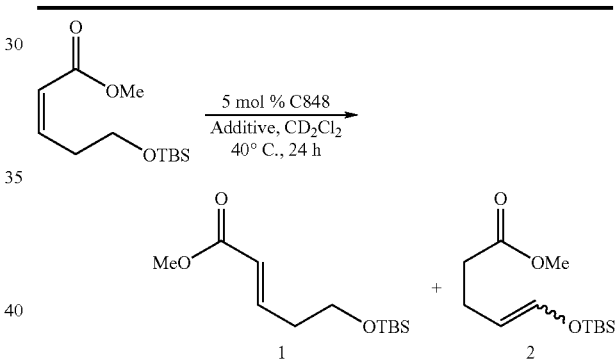

| Isomerization Inhibitor | Product Distribution | |
|---|---|---|
| | 1 | 2 |
| None | 12% | 88% |
| 1 equiv. Maleic Anhydride | None | None |
| 1 equiv. 2,2,2-Trifluoroethanol | 11% | 89% |
| 1 equiv. Nonafluoro-tert-butyl alcohol | 19% | 81% |
| 1 equiv. Phenol | 17% | 83% |
| 1 equiv. Acetic Acid | >95% | None |
| 10 mol % Tricyclohexyl phosphine oxide | 22% | 78% |
| 10 mol % 1,4-Benzoquinone | >95% | None |

Analytical Information (E)-5-tert-butyldimethylsilyloxy-2-pentenoate (1)

$^1H$ NMR ($CD_2Cl_2$): δ6.96 (td, 1H, J=7.2, 15.6 Hz), 5.88 (td, 1H, J=1.5, 15.6 Hz), 3.74 (t, 2H, J=6.5 Hz), 3.70 (s, 3H), 2.41 (td, 2H, J=6.5, 7.2 Hz), 0.90 (s, 9H), 0.06 (s, 6H).

(Z) & (E) mixture of 5-tert-butyldimethylsilyloxy-4-pentenoate (E/Z=1:2) (2). (Ohba, T.; Ikeda, E.; Tsuchiya, N.; Nishimura, K.; Takei, H. *Bioorg. Med. Chem. Lett.* 1996, 6, 2629-2634.)

$^1$H NMR(CD$_2$Cl$_2$): δ6.30 (td, 1H, J=1.5, 12.3 Hz, E), 6.22 (dd, 1H, J=2.4, 6.0 Hz, Z), 4.95 (td, 1H, 7.4, 12.0 Hz, E), 4.47 (dt, 1H, J=6.0, 7.0 Hz, Z), 2.40~2.15 (m, 8H, E & Z), 3.65 (s, 6H, E & Z), 0.94 (s, 9H, Z), 0.92 (s, 9H, E), 0.15 (s, 6H, Z), 0.13 (s, 6H, E)

Example 2

RCM Reaction of Diallyl ether

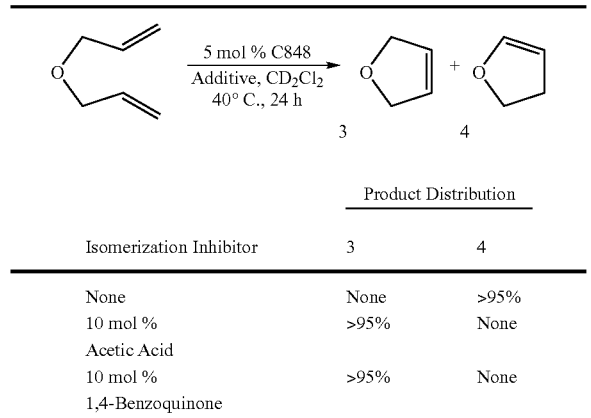

| Isomerization Inhibitor | Product Distribution | |
|---|---|---|
| | 3 | 4 |
| None | None | >95% |
| 10 mol % Acetic Acid | >95% | None |
| 10 mol % 1,4-Benzoquinone | >95% | None |

Analytical Information

2,5 Dihydrofuran (3)

$^1$H NMR (CD$_2$Cl$_2$): δ5.91 (t, 2H, J=0.9 Hz), 4.60 (d, 4H, J-0.9 Hz)

2,3-Dihydrofuran (4)

$^1$H NMR (CD$_2$Cl$_2$): δ6.32 (m, 1H), 4.95(m, 1H), 4.28 (t, 2H, J=9.6 Hz), 2.59 (m, 21H)

Example 3

Self-metathesis reaction of (Z) 1,4-Bis(tert-butyldimethylsilyloxy)-2-butene

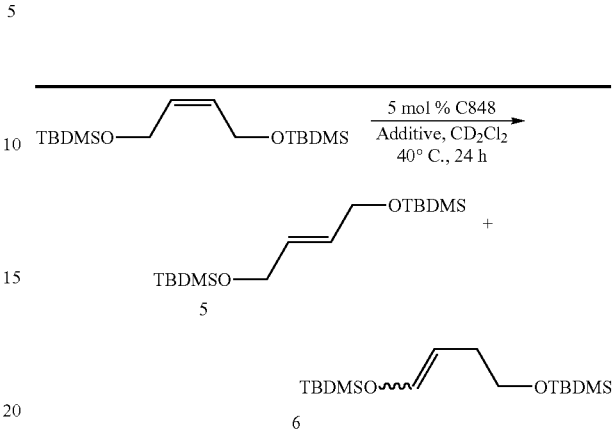

| Isomerization Inhibitor | Product Distribution | |
|---|---|---|
| | 5 | 6 |
| None | None | >95% |
| 10 mol % Acetic acid | None | >95% |
| 10 mol % 1,4-Benzoquinone | >95% | None |

Analytical Information

(E)-1,4-Bis(tert-butyldimethylsilyloxy)-2-butene (5)

$^1$H NMR (CD$_2$Cl$_2$): δ 5.77 (t, 2H, J=3.0 Hz), 4.18 (d, 4H, J=3.0 Hz), 0.92 (s, 9H), 0.08 (s, 6H)

(Z) & (E) mixture of 1,4-Bis(tert-butyldimethylsilyloxy)-1-butene (E/Z=1:2.3) (6). (Kang, K.; Weber, W. P. *Tetrahedron Lett.* 1985, 26, 5753-5754.)

$^1$H NMR (CD$_2$Cl$_2$): δ6.29 (td, 1H, 1.2, 12.1 Hz, E), 6.22 (td, 1H, J=1.5, 5.7 Hz, Z), 4.95 (td, 1H, J=7.2, 12.1 Hz, E), 4.49 (dt, 1H, J=5.7, 7.2 Hz, Z), 3.60 (t, 2H, J=6.9 Hz, Z), 3.57 (t, 2H, J=6.6 Hz, E), 2.30 (td, 2H, J=6.9, 7.2 Hz, Z), 2.09 (td, 2H, J=6.6, 7.2 Hz, E), 0.94 (s, 9H, Z), 0.91 (s, 9H, E), 0.15 (s, 6H, E), 0.07 (s, 6H, Z)

Example 4

Ethenolysis of 11-Eicosenyl Acetate with C823 (0.3 mol %) and 1,4-Benzoquinone (0.6 mol %)

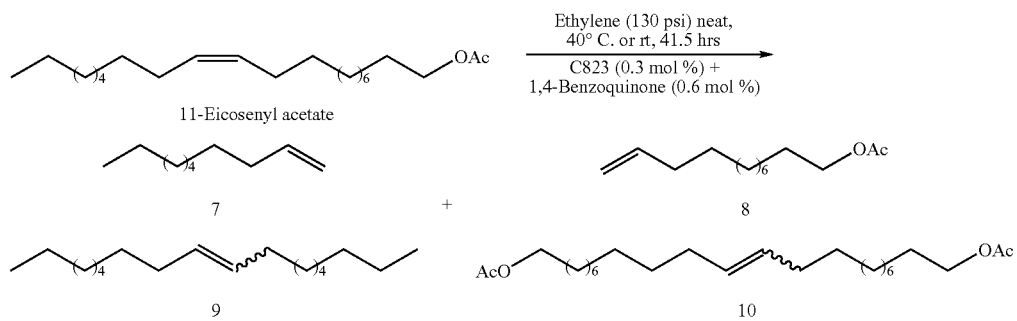

Experimental Procedure:

11-Eicosenyl acetate was degassed with anhydrous Argon for 10 minutes followed by adding 8 g (23.7 mmol) each into two Fisher-Porter bottles. To one bottle was added 1,4-benzoquinone (15 mg, 0.14 mmol) followed by ruthenium catalyst 823 (59 mg, 0.071 mmol) at room temperature. To the other bottle was added only catalyst 823 (59 mg), as the control reaction. Both bottles were pressured with ethylene (130 psi) and stirred for 41.5 hrs at 40° C. or room temperature. During the reaction, samples were collected and analyzed. Samples were quenched with an excess amount of 1 M THMP solution (trishydroxymethyl phosphine in IPA) at ~50° C. for 1 h, then analyzed by GC and GC-MS.

Ethenolysis of 11-Eicosenyl acetate Results
(Reported as Percent GC Area)

Experimental Procedure:

Methyl Oleate (99% pure) was degassed with anhydrous Argon for 10 minutes followed by adding 12 g (40.5 mmol) each to two Fisher-Porter bottles. To one bottle was added 1,4-benzoquinone (9 mg, 0.082 mmol) followed by ruthenium catalyst C823 (33 mg, 0.041 mmol) or C712 (29 mg, 0.041 mmol) at room temperature. To the other bottle was added only catalyst 823 (33 mg) or 712 (29 mg), as the control reaction. Both bottles were pressured with Ethylene (160-150 psi), and stirred for 21.3 hrs at 40° C. During the reaction, the reaction mixture was collected, and then quenched with excess amount of 1 M THMP solution (trishydroxymethyl phosphine in IPA) at ~50° C. for 1 h and analyzed by GC and GC-MS.

| Time (min) | Reaction | 11-Eicosenyl acetate | 1-Decene, 7 | 11-Dodecenyl acetate, 8 | 9-Octadecene, 9 | 11-Docosenyl 1,22-Diacetate, 10 | Isomerization, Impurities |
|---|---|---|---|---|---|---|---|
| 100 | Benzoquinone | 42 | 23 | 32 | 1 | 2 | 0 |
|  | Control | 27 | 28 | 39 | 2 | 3 | 1 |
| 1110 | Benzoquinone | 41 | 22 | 32 | 2 | 2 | 1 |
|  | Control | 23 | 22 | 32 | 3 | 4 | 15 |
| 2490 | Benzoquinone | 41 | 22 | 32 | 2 | 2 | 1 |
|  | Control | 23 | 20 | 28 | 3 | 4 | 21 |

Analytical Information

GC and GC/MS results: Rt 2.10 min (7,1-Decene, $M^+=140$), Rt 9.05 min (8, 11-Dodecenyl acetate, $M^+=226$), Rt 10.96 and Rt 11.03 min (9,9-Octadecene, $M^+=252$), Rt 17.27 min (11-Eicosenyl acetate, $M^+=338$), Rt 30.36 and Rt 31.33 min (10,11-Docosenyl 1,22-Diacetate, $M^+=424$).

Example 5

Ethenolysis of Methyl Oleate, C823 (0.1 mol %)+1,4-Benzoquinone (0.2 mol %)

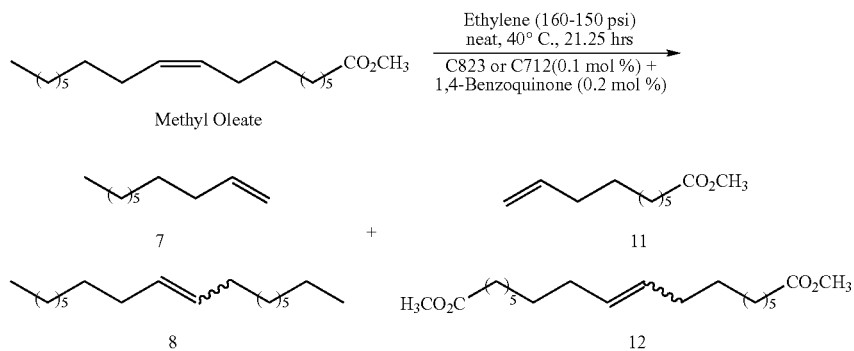

Ethenolysis of Methyl Oleate Results (Reported as Percent GC Area)

| Time (min) | Reaction | Methyl Oleate | 1-Decene, 7 | 9-Methyl Decenoate, 11 | 9-Octadecene, 8 | 1,18-Dimethyl 9-octadendiaote 12 | Isomerization, Impurities |
|---|---|---|---|---|---|---|---|
| 100 | Benzoquinone | 54 | 23 | 24 | 1 | 1 | <1 |
|  | Control | 51 | 21 | 22 | 1 | 1 | <1 |
| 240 | Benzoquinone | 53 | 21 | 23 | 1 | 1 | <1 |
|  | Control | 33 | 30 | 31 | 2 | 2 | 2 |
| 360 | Benzoquinone | 53 | 22 | 22 | 1 | 1 | <1 |
|  | Control | 28 | 31 | 32 | 3 | 3 | 4 |
| 1275 | Benzoquinone | 53 | 21 | 23 | 1 | 1 | <1 |
|  | Control | 27 | 16 | 17 | 3 | 3 | 35 |

Analytical Information

GC and GC/MS results: Rt 2.12 min (7,1-Decene, $M^+$=140), Rt 5.47 min (11, Methyl 9-Decenoate, $M^+$=184), Rt 10.96 and Rt 11.03 min (8,9-Octadecene, $M^+$=252), Rt 14.63 min (Methyl Oleate, $M^+$=296), Rt 17.66 and Rt 17.75 min (12, 1,18-Dimethyl 9-Octadecendioate, $M^+$=340).

Example 6

Ethenolysis of Methyl Oleate, C712 (0.1 mol %)+1,4-Benzoquinone (0.2 mol %)

Experimental Procedure:
Same as described in Example 5 except used 0.1 mol % of C712 in place of C823.

Ethenolysis of Methyl Oleate Results (Reported as Percent GC Area)

| Time (min) | Reaction | Methyl Oleate | 1-Decene, 7 | 9-Methyl Decenoate, 11 | 9-Octadecene, 8 | 1,18-Dimethyl 9-octadendiaote 12 | Isomerization, Impurities |
|---|---|---|---|---|---|---|---|
| 115 | Benzoquinone | 17 | 28 | 28 | 9 | 9 | 8 |
|  | Control | 24 | 17 | 17 | 12 | 12 | 17 |
| 240 | Benzoquinone | 17 | 26 | 26 | 9 | 9 | 12 |
|  | Control | 24 | 17 | 17 | 12 | 12 | 17 |
| 337 | Benzoquinone | 17 | 25 | 25 | 9 | 9 | 14 |
|  | Control | 22 | 18 | 18 | 11 | 11 | 19 |
| 1280 | Benzoquinone | 17 | 21 | 21 | 9 | 9 | 22 |
|  | Control | 21 | 11 | 11 | 11 | 10 | 35 |

Example 7

Ethenolysis of Meadowfoam Oil Methyl Esters, C823 (0.3 mol %)+1,4-Benzoquinone (0.6 mol %)

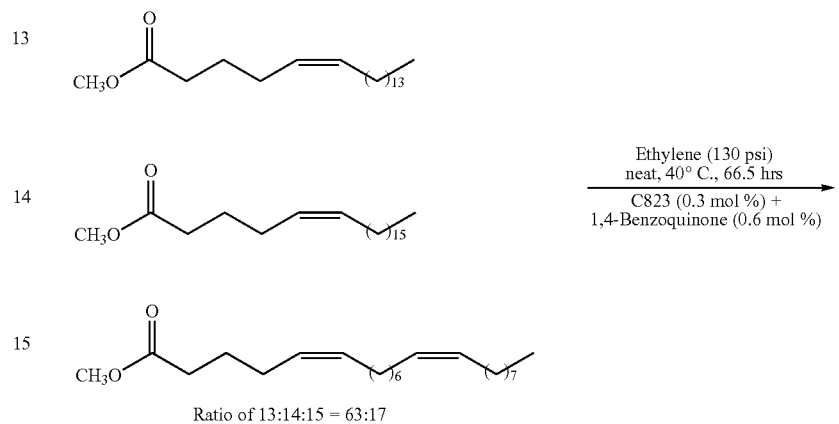

Ratio of 13:14:15 = 63:17

-continued

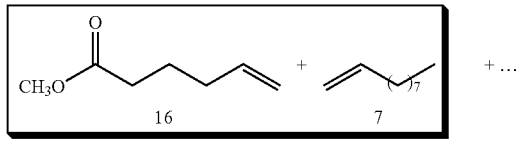

Experimental Procedure:

Meadowfoam oil methyl ester was degassed with anhydrous Argon for 10 minutes followed by adding 10 g (31.3 mmol) to two Fisher-Porter bottles. To one bottles was added 1,4-benzoquinone (20 mg, 0.19 mmol) followed by ruthenium catalyst 823 (77 mg, 0.094 mmol) at room temperature. To the other bottle was added only catalyst 823 (77 mg), as the control reaction. Both bottles were pressured with Ethylene (130 psi), and stirred for 66.5 hrs at 40° C. During the reaction, the reaction mixture was collected, and then quenched with excess amount of 1 M THMP solution (trishydroxymethyl phosphine in IPA) at ~50° C. for 1 h and analyzed by GC and GC-MS.

Ethenolysis of Meadowfoam Oil Methyl Ester
Results (Reported as Percent GC Area)

| Time (hr) | Reaction | Methyl 5-Eicosenoate 13 | 1-Decene, 7 | Methyl 5-hexenoate, 16 | Isomerization, Impurities (rt < 2.5 min) |
|---|---|---|---|---|---|
| 1 | Benzoquinone | 31 | 7 | 10 | 0 |
|   | Control | 39 | 6 | 8 | 0 |
| 3 | Benzoquinone | 30 | 8 | 11 | 0 |
|   | Control | 33 | 7 | 9 | <1 |
| 21.3 | Benzoquinone | 28 | 7 | 11 | <1 |
|   | Control | 31 | 7 | 9 | 1 |
| 66.5 | Benzoquinone | 29 | 7 | 10 | <1 |
|   | Control | 31 | 4 | 5 | 9 |

Analytical Information

GC and GC/MS results: Rt 1.67 min (16, Methyl 5-hexenoate, $M^+$=128), Rt 2.09 min (7,1-Decene, $M^+$=140), Rt 8.88 min (1-Hexadecene, $M^+$=224), Rt 16.39 min (13, Methyl 5-Eicosenoate, $M^+$=324), Rt 18.34 min (15, Methyl 5,13-Docosadienoate, $M^+$=350), Rt 18.65 min (14, Methyl 5-Docosenoate, $M^+$=352).

It is to be understood that while the invention has been described in conjunction with the preferred specific embodiments thereof, the foregoing description is intended to illustrate and not limit the scope of the invention. Other aspects, advantages, and modifications will be apparent to those skilled in the art to which the invention pertains.

All patents, patent applications, journal articles, and other references cited herein are incorporated by reference in their entireties.

We claim:

1. A method for carrying out an olefin metathesis reaction, comprising contacting at least one olefinic reactant with an olefin metathesis catalyst at a temperature in the range of −72° C. to about 20° C. in the presence of an effective amount of an isomerization inhibitor, wherein the olefin metathesis catalyst is a ruthenium alkylidene complex containing an N-heterocyclic carbene ligand coordinated to the ruthenium atom.

2. The method of claim 1, wherein the effective amount of the isomerization inhibitor is effective to reduce the production of unwanted reaction products resulting from olefin isomerization by at least 20% relative to the unwanted reaction products observed when the olefin metathesis reaction is carried out with no isomerization inhibitor.

3. The method of claim 2, wherein the effective amount of the isomerization inhibitor is effective to reduce the production of unwanted reaction products resulting from olefin isomerization by at least 50% relative to the unwanted reaction products observed when the olefin metathesis reaction is carried out with no isomerization inhibitor.

4. The method of claim 1, wherein two olefinic reactants are used.

5. The method of claim 4, wherein one reactant is ethylene.

6. The method of claim 4, wherein one reactant is an α-olefin.

7. The method of claim 1, wherein the isomerization inhibitor is an organic acid.

8. The method of claim 7, wherein the organic acid has a pKa in the range of 1.5 to 6.5 inclusive.

9. The method of claim 8, wherein the organic acid has a pKa in the range of 3.0 to 4.8 inclusive.

10. The method of claim 7, wherein the organic acid has a molecular weight of at most 250 g/mole.

11. The method of claim 10, wherein the organic acid has a molecular weight of at most 175 g/mole.

12. The method of claim 7, wherein the organic acid has the formula $R^{10}$—COOH where $R^{10}$ is selected from H, $C_1$-$C_6$ alkyl, $C_2$-$C_6$ alkenyl, halogenated $C_1$-$C_6$ alkyl, halogenated $C_1$-$C_6$ alkenyl, phenyl, halogenated phenyl, benzyl, and halogenated benzyl.

13. A method for carrying out an ethenolysis reaction, comprising contacting ethylene and at least one additional olefinic reactant with an olefin metathesis catalyst at a temperature in the range of −72° C. to about 20° C. in the presence of a quinone, a substituted quinone, BHT, vitamin E, and/or an organic acid having the formula $R^{10}$—COOH where $R^{10}$ is selected from H, $C_1$-$C_6$ alkyl, $C_2$-$C_6$ alkenyl, halogenated $C_1$-$C_6$ alkyl, halogenated $C_1$-$C_6$ alkenyl, phenyl, halogenated phenyl, benzyl, and halogenated benzyl, wherein the organic acid is present in an amount effective to inhibit olefin isomerization.

14. A method for carrying out an olefin metathesis reaction, comprising contacting an α-olefin and at least one additional olefinic reactant with an olefin metathesis catalyst at a temperature in the range of −72° C. to about 20° C. in the presence of a quinone, a substituted quinone, BHT, vitamin E, andlor an organic acid having the formula $R_{10}$—COOH where $R_{10}$ is selected from H, $C_1$-$C_6$ alkyl, $C_2$-$C_6$ alkenyl, halogenated $C_1$-$C_6$ alkyl, halogenated $C_1$-$C_6$ alkenyl, phenyl, halogenated phenyl, benzyl, and halogenated benzyl, wherein the organic acid is present in an amount effective to inhibit olefin isomerization.

15. An olefin metathesis reaction system, comprising ethylene, a second olefinic reactant, an olefin metathesis catalyst, an isomerization inhibitor acid, and, if an olefin metathesis reaction has begun, at least one ethenolysis product, wherein the second olefin reactant is different from the isomerization inhibitor acid.

16. An olefin metathesis system, comprising an α-olefin, a second olefinic reactant, an olefin metathesis catalyst, an isomerization inhibitor selected from a quinone, a substituted quinone, BHT, vitamin E, andlor an organic acid having the formula $R_{10}$—COOH, and wherein $R_{10}$ is selected from H, $C_1$-$C_6$ alkyl, $C_2$-$C_6$ alkenyl, halogenated $C_1$-$C_6$ alkyl, halogenated $C_1$-$C_6$ alkenyl, phenyl, halogenated phenyl, benzyl, and halogenated benzyl, and, if an olefin metathesis reaction has begun, at least one olefin metathesis product.

17. The method of claim 13, wherein the olefin metathesis catalyst is a ruthenium alkylidene complex containing an N-heterocyclic carbene ligand coordinated to the ruthenium atom.

18. The method of claim 14, wherein the olefin metathesis catalyst is a ruthenium alkylidene complex containing an N-heterocyclic carbene ligand coordinated to the ruthenium atom.

19. The method of claim 15, wherein the olefin metathesis catalyst is a ruthenium alkylidene complex containing an N-heterocyclic carbene ligand coordinated to the ruthenium atom.

20. The method of claim 16, wherein the olefin metathesis catalyst is a ruthenium alkylidene complex containing an N-heterocyclic carbene ligand coordinated to the ruthenium atom.

21. A method for carrying out an olefin metathesis reaction, comprising contacting at least one olefinic reactant with an olefin metathesis catalyst at a temperature in the range of −72° C. to about 20° C. in the presence of an effective amount of an isomerization inhibitor, wherein the effective amount of the isomerization inhibitor is effective to reduce the production of unwanted reaction products resulting from olefin isomerization by at least 20% relative to the unwanted reaction products observed when the olefin metathesis reaction is carried out with no isomerization inhibitor.

22. The method of claim 21, wherein the effective amount of the isomerization inhibitor is effective to reduce the production of unwanted reaction products resulting from olefin isomerization by at least 50% relative to the unwanted reaction products observed when the olefin metathesis reaction is carried out with no isomerization inhibitor.

23. A method for carrying out an olefin metathesis reaction, comprising contacting at least one olefinic reactant with an olefin metathesis catalyst at a temperature in the range of −72° C. to about 20° C. in the presence of an effective amount of an isomerization inhibitor, wherein the isomerization inhibitor is selected from a quinone, a substituted quinone, BHT, vitamin E, andlor an organic acid having the formula $R^{10}$—COOH where $R^{10}$ is selected from H, $C_1$-$C_6$ alkyl, $C_2$-$C_6$ alkenyl, halogenated $C_1$-$C_6$ alkyl, halogenated $C_1$-$C_6$ alkenyl, phenyl, halogenated phenyl, benzyl, and halogenated benzyl.

* * * * *